(12) United States Patent
Saint-Jalmes et al.

(10) Patent No.: US 8,829,236 B2
(45) Date of Patent: Sep. 9, 2014

(54) PROCESS FOR THE PREPARATION OF A HALOGENOACETYL FLUORIDE AND ITS DERIVATIVES

(75) Inventors: Laurent Saint-Jalmes, Vourles (FR); Francois Metz, Irigny (FR)

(73) Assignee: Rhodia Operations, Aubervilliers (FR)

( * ) Notice: Subject to any disclaimer, the term of this patent is extended or adjusted under 35 U.S.C. 154(b) by 380 days.

(21) Appl. No.: 13/386,637

(22) PCT Filed: Jul. 7, 2010

(86) PCT No.: PCT/EP2010/059747
§ 371 (c)(1),
(2), (4) Date: Apr. 6, 2012

(87) PCT Pub. No.: WO2011/009726
PCT Pub. Date: Jan. 27, 2011

(65) Prior Publication Data
US 2012/0190892 A1    Jul. 26, 2012

(30) Foreign Application Priority Data
Jul. 21, 2009 (FR) .................................... 09 03580

(51) Int. Cl.
| | | |
|---|---|---|
| *C07C 51/58* | (2006.01) | |
| *C07C 53/18* | (2006.01) | |
| *C07C 51/64* | (2006.01) | |
| *C07C 51/04* | (2006.01) | |
| *C07C 51/62* | (2006.01) | |

(52) U.S. Cl.
CPC ................ *C07C 51/58* (2013.01); *C07C 51/64* (2013.01); *C07C 51/04* (2013.01); *C07C 51/62* (2013.01)
USPC ............................ 562/541; 562/605; 562/852

(58) Field of Classification Search
CPC ................................ C07C 51/04; C07C 51/62
See application file for complete search history.

(56) References Cited

U.S. PATENT DOCUMENTS

| 5,672,748 | A | * | 9/1997 | Ebmeyer et al. | ............... 562/852 |
| 5,919,341 | A | * | 7/1999 | Braun et al. | ............. 204/157.87 |

FOREIGN PATENT DOCUMENTS

| CN | 1287996 A | 3/2001 |
| GB | 976 316 A | 11/1964 |

OTHER PUBLICATIONS

Markovski, L. N., et al.—"Applications of Dialkylaminosulfur Trifluorides for the Syntheses of Acid Fluorides." Synthesis (1975) vol. 12, pp. 801-802 (2 pages)—XP002563224.
Den, W. et al.—"Photooxidation and biotrickling filtration for controlling indurstrial emissions of trichloroethylene and perchloroethylene." Chemical Engineering Science (2006) vol. 61, No. 24, pp. 7909-7923, Dec. 1, 2006 (15 pages)—XP025011957.
Xun, L. et al.—"The preparation and use of dichloroacetyl chloride." China Chlor-Alkali (Feb. 28, 2001) No. 2—p. 28-29 ; including English translation of Section 1.2 on p. 28 (3 pages).
International Search Report (PCT/ISA/210) issued on Sep. 14, 2010, by European Patent Office as the International Searching Authority for International Application No. PCT/EP2010/059747.

* cited by examiner

*Primary Examiner* — Paul A Zucker
(74) *Attorney, Agent, or Firm* — Beatrice C. Ortego

(57) ABSTRACT

The present invention relates to a method for preparing a halogenoacetyl fluoride and the derivatives thereof. The inventive method for preparing a halogenoacetyl fluoride acid is characterized in that said method includes: a step of preparing a halogenoacetyl halide by photo-oxidation of a halogenoethylene compound in conditions such that the transformation rate of the halogenoethylene compound into halogenoacetyl halide is no higher than 80%, producing a reaction mixture essentially including halogenoacetyl halide and the excess halogenoethylene compound; a step of partial fluorination of the mixture obtained by reacting the latter with hydrofluoric acid suitable for obtaining a mixture of halogenoacetyl fluoride and the excess halogenoethylene compound; a step of separating the halogenoacetyl fluoride and the excess halogenoethylene compound. The invention can be used, specifically, for preparing the trichloroacetyl fluoride used as an intermediate species in the production of trifluoroacetic acid.

53 Claims, No Drawings

PROCESS FOR THE PREPARATION OF A HALOGENOACETYL FLUORIDE AND ITS DERIVATIVES

This application is the United States national phase of PCT/EP2010/059747, filed Jul. 7, 2010, and designating the United States (published in the French language on Jan. 27, 2011, as WO 2011/009726 A1), which claims priority under 35 U.S.C. §119 of FR 0903580, filed Jul. 21, 2009, each hereby expressly incorporated by reference in its entirety and each assigned to the assignee hereof.

A subject-matter of the present invention is a process for the preparation of a haloacetyl fluoride and its derivatives.

The invention relates both to the preparation of a monohaloacetyl fluoride and to the preparation of polyhaloacetyl fluoride.

The invention is also targeted at the use of the haloacetyl fluoride as intermediate in the manufacture of fluroacetyl fluoride, the corresponding fluorocarboxylic acid and derivative.

The invention relates more particularly to the preparation of trichloroacetyl fluoride, which is an intermediate in the manufacture of trifluoroacetyl fluoride, which results in trifluoroacetic acid.

A conventional route for the preparation of trifluoroacetic acid is to hydrolyse trifluoroacetyl fluoride.

A method for the preparation of trifluoroacetyl fluoride described in the literature (GB 976 316) is to carry out the fluorination of trichloroacetyl chloride by reacting the latter with hydrofluoric acid in the presence of a catalyst comprising chromium, generally a chromium(III) oxide.

Trichloroacetyl chloride is a compound which is obtained according to a photooxidation reaction, namely the reaction of tetrachloroethylene (also known as perchloroethylene) with oxygen, in the presence of photons.

The problem which is presented is that this reaction is an extremely slow reaction. The complete conversion of the tetrachloroethylene to trichloroacetyl chloride requires very long reaction times. For example, in order to obtain a virtually complete degree of conversion, a reaction time of greater than approximately one hundred hours is necessary.

When it is desired to achieve high degrees of conversion, a fall in selectivity of the reaction is recorded as the result of the formation of heavy by-products.

Furthermore, at the end of the photooxidation reaction of the tetrachloroethylene, a mixture comprising essentially trichloroacetyl chloride and the excess tetrachloroethylene is obtained. In point of fact, it appears very difficult to separate the said compounds as their boiling points, respectively 121° C. for tetrachloroethylene and 118° C. for trichloroacetyl chloride, are too close to separate them by distillation. Thus, the product used in the following stages is not pure as it is composed of a mixture as defined.

In order to overcome these disadvantages, the Applicant Company provides a process which makes it possible to reduce the duration of the first stage and to obtain a reaction intermediate devoid of its ethylenic precursor.

A first subject-matter of the present invention is a process for the preparation of a haloacetyl fluoride.

Another subject-matter of the invention is a process for the preparation of a fluoroacetyl fluoride involving the haloacetyl fluoride as intermediate.

Another subject-matter of the invention is a process for the preparation of a fluorocarboxylic acid involving the fluoroacetyl fluoride as intermediate.

There has now been found, and it is this which constitutes the subject-matter of the present invention, a process for the preparation of a haloacetyl fluoride, characterized in that it comprises:
 a stage of preparation of a haloacetyl halide by photooxidation of a haloethylenic compound under conditions such that the degree of conversion of the haloethylenic compound to haloacetyl halide is at most equal to 80%, resulting in a reaction mixture comprising essentially the haloacetyl halide and the excess haloethylenic compound,
 a stage of partial fluorination of the mixture obtained by reaction of the mixture with hydrofluoric acid, making it possible to obtain a mixture of haloacetyl fluoride and the excess haloethylenic compound,
 a stage of separation of the haloacetyl fluoride and the excess haloethylenic compound.

Another subject-matter of the invention is a process for the preparation of a fluoroacetyl fluoride from the haloacetyl fluoride obtained above, characterized in that it comprises:
 a second stage of fluorination of the haloacetyl fluoride obtained to give fluoroacetyl fluoride by reaction of the haloacetyl fluoride and hydrofluoric acid, in the gas phase, in the presence of a chromium-based catalyst.

Another subject-matter of the invention is a process for the preparation of a fluorocarboxylic acid from the fluoroacetyl fluoride obtained above, characterized in that it additionally comprises:
 a stage of hydrolysis of the fluoroacetyl fluoride obtained, resulting in a fluorocarboxylic acid.

In the present text, the term "haloethylenic compound" is understood to mean ethylene having from one to four of its hydrogen atoms replaced by a chlorine or bromine atom. It can also be called "chlorinated or brominated ethylenic compound".

The term "haloacetyl" denotes chloroacetyls and bromoacetyls but more preferably chloroacetyls.

The term "halogen" denotes chlorine or bromine and the term "halide" denotes a chloride or a bromide.

More specifically, a subject-matter of the invention is a process for the preparation of a chloro- or bromoacetyl fluoride, characterized in that it comprises:
 a stage of preparation of a chloro- or bromoacetyl chloride or bromide by photooxidation of a chlorinated or brominated ethylenic compound under conditions such that the degree of conversion of the chlorinated or brominated ethylenic compound to give chloro- or bromoacetyl chloride or bromide is at most equal to 80%, resulting in a reaction mixture essentially comprising the chloro- or bromoacetyl chloride or bromide and the excess chlorinated or brominated ethylenic compound,
 a stage of partial fluorination of the mixture obtained by reaction of the mixture with hydrofluoric acid, making it possible to obtain a mixture of chloro- or bromoacetyl fluoride and the excess chlorinated or brominated ethylenic compound,
 a stage of separation of the chloro- or bromoacetyl fluoride and the excess chlorinated or brominated ethylenic compound.

The invention also includes a process for the preparation of a fluoroacetyl fluoride from the choro- or bromoacetyl fluoride obtained above, characterized in that it additionally comprises:
 a second stage of fluorination of the chloro- or bromoacetyl fluoride obtained to give fluoroacetyl fluoride by reaction of the chloro- or bromoacetyl fluoride and hydrofluoric acid, in the gas phase, in the presence of a chromium-based catalyst.

As mentioned above, the invention also includes a process for the preparation of a fluorocarboxylic acid from the fluoroacetyl fluoride obtained above, characterized in that it additionally comprises a stage of hydrolysis of the fluoroacetyl fluoride obtained, resulting in a fluorocarboxylic acid.

A preferred embodiment of the invention consists of a process for the preparation of trifluoroacetic acid, characterized in that it comprises:
 a stage of preparation of trichloroacetyl chloride by photooxidation of tetrachloroethylene under conditions such that the degree of conversion of the tetrachloroethylene to give trichloroacetyl chloride is at most equal to 80%, resulting in a reaction mixture essentially comprising the trichloroacetyl chloride and the excess tetrachloroethylene,
 a stage of partial fluorination of the mixture obtained by reaction of the mixture with hydrofluoric acid, making it possible to obtain a mixture of trichloroacetyl fluoride and the excess tetrachloroethylene,
 a stage of separation of the trichloroacetyl fluoride from the excess tetrachloroethylene,
 a second stage of fluorination of the trichloroacetyl fluoride obtained to give trifluoroacetyl fluoride by reaction of the trichloroacetyl fluoride and hydrofluoric acid, in the gas phase, in the presence of a chromium-based catalyst,
 a stage of hydrolysis of the trifluoroacetyl fluoride obtained.

According to one characteristic of the process of the invention, the preparation of a haloacetyl halide is carried out by photooxidation of a haloethylenic compound.

The haloethylenic compound involved in the process of the invention corresponds more particularly to the following formula:

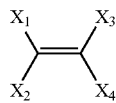

(I)

in which formula:
 $X_1$, $X_2$ and $X_3$ represent a hydrogen atom or a chlorine or bromine atom,
 $X_4$ represents a chlorine or bromine atom.

In the formula (I), at least one of the atoms $X_1$, $X_2$ and $X_3$ preferably represents another chlorine or bromine atom.

Mention may more particularly be made, as examples of compounds corresponding to the formula (I), of vinylidene chloride (1,1-dichloroethylene), trichloroethylene and tetrachloroethylene.

The reaction is advantageously carried out in the vicinity of the boiling point of the reaction medium, generally between 50 and 120° C., under actinic irradiation and under a stream of oxygen for a period of time which may be from 2 to 100 hours.

It is preferable for the oxygen to be introduced in excess, preferably in a proportion of 1 to 10 mol of oxygen per mole of haloacetyl formed. The excess oxygen can optionally be recovered and recycled.

The reaction is advantageously carried out in the absence of water.

According to one characteristic of the process of the invention, the reaction is continued until the degree of conversion of the haloethylenic compound to haloacetyl halide is at most equal to 80%, preferably between 30 and 80% and more preferably still between 60 and 75%.

At the end of the reaction, a mixture is obtained essentially comprising the haloacetyl halide and the excess haloethylenic compound of formula (I).

The haloacetyl halide corresponds to the following formula:

$$X_1X_2X_3C\text{---}COX_4 \qquad (II)$$

in which formula:
 $X_1$, $X_2$, $X_3$ and $X_4$ have the meanings given for the formula (I).

The mixture obtained generally comprises from 20 to 70% by weight of haloacetyl halide and from 70 to 20% by weight of the haloethylenic compound and less than 10% of impurities, such as, for example, the saturated halogenated compound resulting from the halogenation of the haloethylenic compound or the polyhalogenated dimer of the haloethylenic compound.

According to a second stage of the process of the invention, the preparation of haloacetyl fluoride is carried out by carrying out the partial fluorination of the mixture obtained above, which essentially comprises the haloacetyl halide, by reaction of the mixture with liquid hydrofluoric acid.

Although a fluorinating catalyst can be employed, the preferred embodiment of this partial fluorination stage consists in carrying out the reaction in the absence of catalysts.

The amount of hydrofluoric acid, expressed by the ratio of the number of moles of hydrofluoric acid to the number of moles of haloacetyl halide, is advantageously chosen between 1 and 10. The said ratio if preferably between 1 and 5.

The fluorination reaction is carried out at a temperature preferably chosen between 80° C. and 150° C. and more preferably between 100° C. and 120° C.

The reaction is carried out under autogenous pressure of the reactants, which is adjusted between 1 and 100 bar (absolute) and preferably between 5 and 30 bar, so as to remove the hydrohalic acid (generally hydrochloric acid) formed during the reaction.

The reaction is carried out under an atmosphere of inert gases, preferably under a nitrogen atmosphere.

At the end of the reaction, a two-phase medium is obtained. One of the phases is composed of the excess hydrofluoric acid and the other phase is an organic phase which comprises the haloacetyl fluoride and the unreacted haloethylenic compound.

The two phases are separated according to conventional separation techniques, such as, for example, separation by settling.

The recovered upper phase comprises hydrofluoric acid, which can be recycled to the fluorination stages.

The lower phase is an organic phase.

The composition of the organic phase can vary but preferably comprises from 50 to 80% by weight of haloacetyl fluoride and from 50 to 20% by weight of haloethylenic compound.

The preferred composition of the organic phase is from 60 to 70% by weight of haloacetyl fluoride and from 40 to 30% by weight of haloethylenic compound.

In a following stage, a distillation operation is carried out which makes it possible to separate the haloacetyl fluoride and the haloethylenic compound.

The abovementioned organic phase, comprising the compounds to be separated, is introduced into a distillation column, where hydrofluoric acid is removed at the distillation top, then the compound having the lower boiling point between the haloacetyl fluoride and the haloethylenic compound is removed at the distillation top and the compound having the higher boiling point is recovered at the distillation bottom.

Distillation is carried out at a temperature in the reboiler generally greater by from 20° C. to 50° C. than the boiling point of the compound removed at the distillation top and under a pressure of between 400 mbar and 10 bar, preferably in the vicinity of 1 bar.

Distillation is carried out in a conventional distillation apparatus.

A person skilled in the art is fully in a position to choose the means to be employed according to the compounds to be separated.

The following will simply be restated. The size (in particular the diameter) of the distillation columns depends on the circulating stream and on the internal pressure. Their dimensions will thus be arranged mainly according to the flow rate of mixture to be treated. The internal parameter which is the number of theoretical stages is determined in particular by the purity of the starting compound and the purity of the product which has to be obtained at the distillation top.

It will be specified that the columns can be packed without distinction with plates or with stacked packing, as is fully known to a person skilled in the art.

The plant being determined, a person skilled in the art adjusts the operating parameters of the column.

Thus, the distillation column can advantageously, but not limitingly, be a column having the following specifications:
  number of theoretical stages: from 1 to 10, preferably from 1 to 5,
  reflux rate R between 1 and 50, preferably between 10 and 20.

At the column bottom, the distillation residue is recovered which comprises, as the case may be, the haloacetyl fluoride or the haloethylenic compound and, at the column top, a gas phase is recovered composed of the hydrofluoric acid and then of the haloacetyl fluoride or the haloethylenic compound.

The gas phase is cooled and is converted into liquid form by cooling at a temperature, for example, of between −20° C. and 10° C., preferably of between −10° C. and 0° C.

This operation is carried out by passing through a condenser which is a conventional device, for example a tubular exchanger, fed with water or with a fluid maintained at a temperature in the vicinity of the chosen cooling temperature.

Thus, either the haloethylenic compound or the haloacetyl fluoride is obtained at the distillation bottom.

The haloethylenic compound is recycled and the haloacetyl fluoride obtained is subsequently treated.

In the case of the separation of trichloroacetyl fluoride from tetrachloroethylene, the hydrofluoric acid and then the trichloroacetyl fluoride are recovered at the distillation top and the tetrachloroethylene is recovered at the distillation bottom and can be recycled to the first stage of the process.

According to one characteristic of the process of the invention, the preparation of fluoracetyl fluoride is carried out by reaction of the haloacetyl fluoride and hydrofluoric acid, in the gas phase, in the presence of a chromium-based catalyst.

A chromium-based fluorination catalyst is involved in the process of the invention.

The catalyst used preferably comprises oxides, halides, oxyhalides or inorganic salts of chromium optionally doped with a metal element, such as, for example, nickel, cobalt, magnesium and zinc.

It is preferably an oxide of chromium, a fluoride of chromium or an oxyfluoride of chromium or else chromium doped with a metal element, such as, for example, nickel and magnesium.

The catalyst can be subjected to an activation by heat treatment and/or a fluorination treatment. In particular, the activation can take place during the fluorination. The temperature is advantageously chosen between 100° C. and 400° C., preferably between 200° C. and 300° C.

Use is made in particular of chromium in the form of oxides in different oxidation states and/or in the form of hydroxides, in the powder or gel form.

Use may be made of an activated chromium(III) oxide prepared, for example, by precipitation of water-soluble chromium(III) salts, such as, for example, chlorides, nitrates, acetates or sulphates, using an alkali metal hydroxide, preferably sodium hydroxide or potassium hydroxide, or ammonium hydroxide. The precipitate is dried at approximately 110° C. and calcined at a temperature below 700° C., preferably between 400 and 600° C.

Anhydrous chromium oxide can be obtained by calcination of inorganic chromium salts, such as ammonium chromate or chromium nitrate, or by calcination of organic chromium salts, such as, for example, chromium oxalates or formates, at 350° C., under a nitrogen atmosphere.

Recourse may in particular be had to a catalyst of Cr—Ni type, with a valency of the chromium of between 2 and 3 and a valency of the nickel of between 0 and 2, the amount of nickel, expressed as atom %, representing from 0.1 to 10%.

A method for the preparation of this catalyst consists in thermally decomposing, separately or as a mixture, one or more organic chromium salts (for example oxalate) and a salt or several salts of nickel (for example oxalate), shaping the mixture and then fluorinating the shaped catalyst.

The thermal decomposition generally takes place between 370° C. and 400° C., under an inert gas atmosphere, for example nitrogen.

The shaping of the catalyst obtained can be carried out, under non-oxidizing conditions, for example by extrusion, then the shaped product is dried at approximately 120° C.-130° C. and then calcined at 370° C.-400° C., under an inert atmosphere.

The catalyst is heated between 100° C. and 500° C., under hydrofluoric acid, for between 1 and 12 hours.

A catalyst of Cr—Mg type can also be employed.

It can be obtained in particular by mixing a chromium salt (for example nitrate) in solution with a magnesium oxide or hydroxide, prolonged drying between 12 and 24 hours, for example at 100° C., and then activating with hydrofluoric acid, for example at 200° C.

The active phase can be introduced in a finely divided form or else shaped or deposited on a support.

Mention may be made, as examples of supports, of silica, alumina, zirconia or titanium oxide. Preferably, the chromium is deposited on a support in a proportion of from 0.5% to 5% of the weight of the catalyst.

The catalysts can be provided in different forms in the process of the invention: powder, shaped products, such as granules (for example extrudates or beads) or pellets, which are obtained by extrusion, moulding, compacting or any other type of known process. In practice, at the industrial level, it is the granule or bead forms which are most advantageous, both with regard to efficiency and with regard to convenience of use.

In accordance with the process of the invention, the fluorination reaction is carried out by reacting the haloacetyl fluoride and hydrofluoric acid, in the gas phase, in the presence of the fluorination catalyst.

The ratio of hydrofluoric acid to the haloacetyl fluoride can vary widely. Generally, the amount of hydrofluoric acid is in excess. Thus, the ratio of the number of moles of hydrofluoric acid to the number of moles of haloacetyl fluoride generally varies between 1 and 20. It is advantageously chosen between 6 and 8.

The process in accordance with the invention is carried out at a high temperature, generally of greater than 200° C. It is recommended to operate at temperatures of between 250° C. and 400° C., preferably of between 250° C. and 300° C.

For reasons of simplicity, the process of the invention is carried out at atmospheric pressure. However, it is also possible to operate under lower or higher pressures.

From a practical viewpoint, the process can be carried out batchwise or continuously.

The starting point is the mixing, in any way, of the haloacetyl fluoride and the hydrofluoric acid.

Thus, the said reactants can be mixed, in a mixing region, and then the mixture obtained can be sent to the catalytic bed.

When the process is carried out batchwise, the amount of fluorination catalyst employed, expressed as weight of catalyst per weight of the haloacetyl fluoride, can vary, for example, between 0.5 and 20%, preferably between 0.5 and 5%.

The other alternative form of the invention consists in carrying out the reaction continuously, in a tubular reactor comprising the solid catalyst positioned at the fixed bed.

The haloacetyl fluoride and the hydrofluoric acid can be introduced separately or as a mixture into the reactor. As mentioned above, they can be mixed in a mixing region and then the mixture obtained can be sent to the catalytic bed.

The reaction mixture passes through the catalytic bed, preferably from the bottom upwards.

The contact time, which is defined as the ratio of the apparent volume of catalyst to the flow rate of the gas stream, can vary widely and is generally between 0.2 and 100 seconds. The contact time is preferably chosen between 5 and 50 seconds.

The weight of substrate employed per weight of catalyst and per hour generally varies between $0.01\ h^{-1}$ and $2\ h^{-1}$, preferably between $0.05\ h^{-1}$ and $0.5\ h^{-1}$.

At the end of the reaction, a gas phase is recovered which comprises the fluoroacetyl fluoride, the excess hydrofluoric acid and the hydrohalic acid (preferably hydrochloric acid) formed by the reaction.

According to an alternative form of the invention, the fluoroacetyl fluoride can be recovered from the said gas stream, comprising the fluoroacetyl fluoride, the hydrofluoric acid and the hydrohalic acid, by condensing the said gas stream by lowering its temperature to between −40° C. and 10° C., preferably between −20° C. and 0° C., and by then distilling the condensed stream.

In accordance with the process of the invention, a stage of hydrolysis of the fluoroacetyl fluoride to give fluorocarboxylic acid is subsequently carried out.

To this end, the gas stream is brought into contact with water. The amount of water employed is at least equal to the stoichiometric amount.

Generally, the operation is carried out by sending the gas stream into a hydrolysis column, the water being sent countercurrentwise to the gas stream, which rises from the bottom upwards in the column.

An acid hydrolysis can also be carried out, for example by resorting to a solution of a strong inorganic acid, for example 30% by weight hydrochloric acid.

Thus, the fluorocarboxylic acid is recovered at the column bottom and the gaseous hydrochloric acid is recovered at the column top.

The salts of the fluorocarboxylic acids can be easily manufactured from the acid, in particular by reaction with a base, preferably sodium hydroxide or potassium hydroxide.

The process of the invention is advantageously carried out in equipment capable of withstanding the corrosion brought about by the hydrofluoric acid. To this end, materials are chosen for the part in contact with the reaction medium which are resistant to corrosion, such as alloys based on molybdenum, chromium, cobalt, iron, copper, manganese, titanium, zirconium, aluminium, carbon and tungsten, sold under the Hastelloy® brands, or nickel, chromium, iron or manganese alloys with the addition of copper and/or molybdenum, sold under the Inconel® name, and more particularly the alloys Hastelloy C 276 or Inconel 600, 625 or 718.

It is also possible to chose stainless steels, such as austenitic steels [Robert H. Perry et al., *Perry's Chemical Engineers' Handbook, Sixth Edition* (1984), pages 23-44] and more particularly stainless steels 304, 304 L, 316 or 316 L. Use is made of a steel having a nickel content of at most 22% by weight, preferably of between 6 and 20% by weight and more preferably of between 8 and 14% by weight.

The steels 304 and 304 L have a nickel content varying between 8 and 12% and the steels 316 and 316 L have a nickel content varying between 10 and 14%.

All of the various stages of the process of the invention can be carried out continuously or batchwise.

The process of the invention is particularly advantageous as it exhibits numerous advantages.

The first stage of the process, which requires a limitation on the degree of conversion of the haloethylenic compound, makes it possible to benefit with regard to the duration of the reaction and with regard to the selectivity of the reaction.

Furthermore, due to a shorter reaction time, the fluorination of the haloethylenic compound is prevented. Specifically, for example, the tetrachloroethylene is fluorinated and forms a chlorofluorocarbon CFC compound, regarded as a greenhouse gas.

The process of the invention makes it possible, at the end of the first fluorination stage, to separate the haloacetyl fluoride obtained from the excess haloethylenic compound, which makes it possible to charge a purer product in the continuation of the process.

Furthermore, the second fluorination stage requires less hydrofluoric acid.

The examples which follow illustrate the invention without, however, limiting it.

The abbreviations have the following meanings:
TCAC: trichloroacetyl chloride
TCAF: trichloroacetyl fluoride
TFAF: trifluoroacetyl fluoride
TFA: trifluoroacetic acid
PER: perchloroethylene (or tetrachloroethylene).

In the examples, the degree of conversion and the yields obtained are defined.

The degree of conversion (DC) corresponds to the ratio of the number of moles of substrate TCAC converted to the number of moles of substrate TCAC charged The yield (CY) corresponds to the ratio of the number of moles of product TCAF formed to the number of moles of substrate CTAC converted.

EXAMPLE 1

500 g of PER are introduced into a 2 liter jacketed Pyrex reactor equipped with a condenser (−10° C.) and a mercury vapour lamp and are brought to reflux (110° C.) under irradiation (210-260 nm) and under a gas stream composed of a mixture of pure oxygen (4 l/h) and of nitrogen (0.5 l/h).

The gas chromatography analysis (catharometric detection) of the reaction medium after reacting for 4 h indicates the presence of 74% of TCAC and of 26% of PER (percentages by weight).

210.6 g (0.86 mol) of a TCAC/PER (74/26 w/w) mixture and 40 g (2 mol) of anhydrous hydrofluoric acid are introduced into a 0.3 liter Hastelloy® C276 autoclave cooled to 0° C.

The reactor is subsequently heated to 120° C. (rise in temperature of approximately 1 h) and then maintained at 120° C. for 5 h under autogenous pressure (the pressure being approximately 60 bar).

The reactor is subsequently cooled to 0° C. (residual pressure of approximately 15 bar) and then the reaction medium is slowly withdrawn into a polyfluoroethylene flask cooled to −30° C.

The two-phase reaction medium is then degassed at 20° C. with stirring to remove HCl and HF present.

After degassing, the homogeneous reaction medium is analysed by quantitative gas chromatography to give the following results:
$DC_{TCAC}$: 89%
$CY_{TCAF}$: 92%.

The final crude reaction medium obtained is composed of two phases, the compositions of which are as follows:
upper phase:
HF=94 mol %
TCAF=1.5 weight %
PER=0.07 weight % (i.e., 0.25% of the initial PER)
TCAC=HCl=0%
lower phase:
HF=1 weight %
TCAF=98.5 mol %
PER=93% of the initial PER
TCAC=7% of the initial TCAC
HCl=1.1 weight %.

The aqueous and organic phases are separated, after separation by settling.

The TCAF is recovered from the lower organic phase by distillation at atmospheric pressure.

The mixture of the hydrohalic acids and then the TCAF, which distills at 69° C., are recovered at the distillation top.

The PER is found in the distillation bottom with the unreacted TCAC.

The TCAF is fluorinated.

Predistilled trichloroacetyl fluoride (TCAF) and anhydrous HF are introduced, at respective flow rates of 20 g/h and from 20 to 50 g/h, into a Hastelloy C276 reactor composed of a tube with a length of 60 cm and an external diameter of 2.5 cm filled with a catalyst based on chromium oxide (~150 g) dried beforehand to constant weight and fluorinated (24 hours at 250° C.).

The temperature is set at 250-300° C.

Under these conditions, the residence time $t_R$ varies between 10 and 20 s.

The trifluoroacetyl fluoride is obtained with a yield by weight of 90%.

The trifluoroacetyl fluoride is hydrolysed to give trifluoroacetic acid using water acidified with HCl.

The yield of the hydrolysis reaction is greater than 90% by weight.

EXAMPLES 2 TO 4

The following examples relating to the fluorination of TCAC to give TCAF were carried out under the same general conditions (temperature=120° C.); only the parameters which vary are mentioned in Table (I) below.

In Examples 3 and 4, the reaction is carried out under autogenous pressure whereas, in Example 4, the pressure is regulated at 22 bar.

The results obtained are recorded in the following table:

TABLE I

| Ex. | TCAC/PER (g) | HF/TCAC eq. | t (h) | Final pressure at 120° C. (bar) | $DC_{TCAC}$ % | $DC_{PER}$ % | $CY_{TCAF}$ % |
|---|---|---|---|---|---|---|---|
| 2 | 211 | 2.3 | 6 | 35 | 86 | 8.5 | 87 |
| 3 | 244 | 1.3 | 6 | 63 | 81 | 7 | 94 |
| 4 | 217 | 2.3 | 5 | regulated at 22 bar | 80 | 15 | 90 |

The invention claimed is:

1. A process for preparing a halogenoacetyl fluoride, the process comprising:
   step 1)—preparing a halogenoacetyl halide by photooxidation of a chlorinated or brominated ethylenic compound under conditions such that said chlorinated or brominated ethylenic compound is converted to said halogenoacetyl halide with a conversion of at most equal to 80%, resulting in a reaction mixture comprising said halogenoacetyl halide and excess chlorinated or brominated ethylenic compound, wherein the halogenoacetyl in said halogenoacetyl halide is selected from the group consisting of chloroacetyls and bromoacetyls, and wherein the halide in said halogenoacetyl halide is a chloride or a bromide;
   step 2)—partially fluorinating said reaction mixture obtained by said step 1) by reaction of said reaction mixture with hydrofluoric acid, to obtain a mixture of halogenoacetyl fluoride and said excess chlorinated or brominated ethylenic compound, wherein the halogenoacetyl in said halogenoacetyl fluoride is selected from the group consisting of chloroacetyls and bromoacetyls; and
   step 3)—separating said halogenoacetyl fluoride from said excess chlorinated or brominated ethylenic compound.

2. A process for preparing a fluoroacetyl fluoride, the process comprising:
   step 1)—preparing a halogenoacetyl halide by photooxidation of a chlorinated or brominated ethylenic compound under conditions such that said chlorinated or brominated ethylenic compound is converted to said halogenoacetyl halide with a conversion of at most equal to 80%, resulting in a reaction mixture comprising said halogenoacetyl halide and excess chlorinated or brominated ethylenic compound, wherein the halogenoacetyl in said halogenoacetyl halide is selected from the group consisting of chloroacetyls and bromoacetyls, and wherein the halide in said halogenoacetyl halide is a chloride or a bromide;
   step 2)—partially fluorinating said reaction mixture obtained by said step 1) by reaction of said reaction mixture with hydrofluoric acid, to obtain a mixture of halogenoacetyl fluoride and said excess chlorinated or brominated ethylenic compound, wherein the halogenoacetyl in said halogenoacetyl fluoride is selected from the group consisting of chloroacetyls and bromoacetyls;

step 3)—separating said halogenoacetyl fluoride from said excess chlorinated or brominated ethylenic compound; and step 4)—fluorinating said halogenoacetyl fluoride obtained in said step 3) to form fluoroacetyl fluoride by reaction of said halogenoacetyl fluoride obtained in said step 3) and hydrofluoric acid, in a gas phase, with a chromium-based catalyst present.

3. A process for preparing a fluorocarboxylic acid, the process comprising:
step 1)—preparing a halogenoacetyl halide by photooxidation of a chlorinated or brominated ethylenic compound under conditions such that said chlorinated or brominated ethylenic compound is converted to said halogenoacetyl halide with a conversion of at most equal to 80%, resulting in a reaction mixture comprising said halogenoacetyl halide and excess chlorinated or brominated ethylenic compound, wherein the halogenoacetyl in said halogenoacetyl halide is selected from the group consisting of chloroacetyls and bromoacetyls, and wherein the halide in said halogenoacetyl halide is a chloride or a bromide;
step 2)—partially fluorinating said reaction mixture obtained by said step 1) by reaction of said reaction mixture with hydrofluoric acid, to obtain a mixture of halogenoacetyl fluoride and said excess chlorinated or brominated ethylenic compound, wherein the halogenoacetyl in said halogenoacetyl fluoride is selected from the group consisting of chloroacetyls and bromoacetyls;
step 3)—separating said halogenoacetyl fluoride from said excess chlorinated or brominated ethylenic compound;
step 4)—fluorinating said halogenoacetyl fluoride obtained in said step 3) to form fluoroacetyl fluoride by reaction of said halogenoacetyl fluoride obtained in said step 3) and hydrofluoric acid, in a gas phase, with a chromium-based catalyst present; and
step 5)—hydrolyzing said fluoroacetyl fluoride obtained in said step 4), resulting in forming a fluorocarboxylic acid.

4. The process according to claim 1, wherein said chlorinated or brominated ethylenic compound corresponds to the following formula (I):

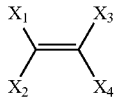

(I)

wherein, in said formula (I),
$X_1$, $X_2$ and $X_3$ represent a hydrogen atom, a chlorine atom or bromine atom, and
$X_4$ represents a chlorine atom or bromine atom.

5. The process according to claim 4, wherein said chlorinated or brominated ethylenic compound is vinylidene chloride, trichloroethylene or tetrachloroethylene.

6. The process according to claim 1, wherein the conversion of said chlorinated or brominated ethylenic compound to said halogenoacetyl halide in said step 1) is between 30% and 80%.

7. The process according to claim 1, wherein said reaction mixture obtained in said step 1) comprises from 20% to 70% by weight of said halogenoacetyl halide, from 70% to 20% by weight of said chlorinated or brominated ethylenic compound, and less than 10% of impurities.

8. The process according to claim 1, wherein said partial fluorination of said reaction mixture obtained in said step 1) is carried out in said step 2) by reaction of said reaction mixture with liquid hydrofluoric acid, with a molar ratio of said hydrofluoric acid to said halogenoacetyl halide between 1 and 10.

9. The process according to claim 8, wherein said partial fluorination reaction is carried out in step 2) at a temperature of 80° C. to 150° C. under autogenous pressure of reactants of said fluorination reaction.

10. The process according to claim 8, wherein, at the end of said partial fluorination reaction, a two-phase mixture which includes an organic phase is obtained, wherein said organic phase comprises from 50% to 80% by weight, of said halogenoacetyl fluoride and from 50% to 20% by weight, of said chlorinated or brominated ethylenic compound.

11. The process according to claim 1, wherein a distillation operation is carried out in said step 3) to separate said halogenoacetyl fluoride from said excess chlorinated or brominated ethylenic compound, and wherein said chlorinated or brominated ethylenic compound is optionally recycled to said step 1).

12. The process according to claim 2, wherein said fluorination of said halogenoacetyl fluoride is carried out in said step 4) by reaction of said halogenoacetyl fluoride with hydrofluoric acid with a fluorination catalyst present and with a molar ratio of said hydrofluoric acid to said halogenoacetyl fluoride from 1 to 20.

13. The process according to claim 12, wherein said fluorination catalyst comprises an oxide, a halide, an oxyhalide or an inorganic salt of chromium optionally doped with a metal element.

14. The process according to claim 13, wherein said fluorination catalyst comprises an oxide of chromium, a fluoride of chromium, an oxyfluoride of chromium or chromium doped with a metal element.

15. The process according to claim 12, wherein said fluorination catalyst is subjected to activation by a treatment selected from the group consisting of heat treatment, a fluorination treatment, and combination thereof, said activation optionally taking place during said fluorination of said halogenoacetyl fluoride in said step 4).

16. The process according to claim 12, wherein said fluorination catalyst is a chromium(III) oxide.

17. The process according to claim 12, wherein the temperature of the fluorination reaction in said step 4) is from 250° C. to 400° C.

18. The process according to claim 12, wherein mixing of said halogenoacetyl fluoride and said hydrofluoric acid is carried out in a mixing region to form a reactants mixture, and then wherein the obtained reactants mixture is sent to a catalytic bed.

19. The process according to claim 12, wherein contact time, defined as a ratio of apparent volume of catalyst to gaseous flow rate, varies from 0.2 seconds to 100 seconds in said fluorinaton reaction of said step 4).

20. The process according to claim 12, wherein the weight of substrate employed per weight of catalyst and per hour varies from 0.01 $h^{-1}$ to 2 $h^{-1}$ in said fluorinaton reaction of said step 4).

21. The process according to claim 12, wherein, at the end of said fluorination reaction in said step 4), a gas stream is recovered, said recovered gas stream comprising said fluoroacetyl fluoride, excess hydrofluoric acid and hydrohalic acid formed by said fluorination reaction.

22. The process according to claim 21, wherein a step 5) of hydrolysis of said fluoroacetyl fluoride to give fluorocarboxylic acid is subsequently carried out by bringing said gas stream into contact with water.

23. The process according to claim 21, wherein the fluoroacetyl fluoride is recovered from said gas stream comprising the fluoroacetyl fluoride, the hydrofluoric acid and the hydrohalic acid by condensing said gas stream by lowering its temperature to a value of from −40° C. to 10° C. to form a condensed stream, and by then distilling said condensed stream.

24. The process according to claim 1, being carried out to prepare trifluoroacetic acid from trichloroacetyl fluoride obtained in said step 3), wherein:
in said step 1), trichloroacetyl chloride is prepared by photooxidation of tetrachloroethylene under conditions such that the tetrachloroethylene is converted to give trichloroacetyl chloride with a conversion of at most equal to 80%, resulting in a reaction mixture comprising the trichloroacetyl chloride and excess tetrachloroethylene,
in said step 2), the reaction mixture obtained in said step 1) is partially fluorinated by reacting said reaction mixture with hydrofluoric acid, to obtain a mixture of trichloroacetyl fluoride and excess tetrachloroethylene,
in said step 3), the trichloroacetyl fluoride is separated from the excess tetrachloroethylene, and
wherein said process further comprises:
step 4)—fluorinating the trichloroacetyl fluoride obtained in said step 3) to give trifluoroacetyl fluoride by reaction of the trichloroacetyl fluoride and hydrofluoric acid, in a gas phase, with a chromium-based catalyst present, and
step 5)—hydrolyzing the trifluoroacetyl fluoride obtained in said step 4) to form trifluoroacetic acid.

25. The process according to claim 22, wherein the fluorocarboxylic acid obtained by said hydrolysis in said step 5) is reacted with a base.

26. The process according to claim 2, wherein the conversion of said chlorinated or brominated ethylenic compound to said halogenoacetyl halide in said step 1) is from 30% to 80%.

27. The process according to claim 3, wherein the conversion of said chlorinated or brominated ethylenic compound to said halogenoacetyl halide in said step 1) is from 30% to 80%.

28. The process according to claim 2, wherein said reaction mixture obtained in said step 1) comprises from 20% to 70% by weight of said halogenoacetyl halide, from 70% to 20% by weight of said chlorinated or brominated ethylenic compound, and less than 10% of impurities.

29. The process according to claim 3, wherein said reaction mixture obtained in said step 1) comprises from 20% to 70% by weight of said halogenoacetyl halide, from 70% to 20% by weight of said chlorinated or brominated ethylenic compound, and less than 10% of impurities.

30. The process according to claim 2, wherein said partial fluorination of said reaction mixture obtained in said step 1) is carried out in said step 2) by reaction of said reaction mixture with liquid hydrofluoric acid, with a molar ratio of said hydrofluoric acid to said halogenoacetyl halide between 1 and 10.

31. The process according to claim 3, wherein said partial fluorination of said reaction mixture obtained in said step 1) is carried out in said step 2) by reaction of said reaction mixture with liquid hydrofluoric acid, with a molar ratio of said hydrofluoric acid to said halogenoacetyl halide between 1 and 10.

32. The process according to claim 2, wherein a distillation operation is carried out in said step 3) to separate said halogenoacetyl fluoride from said chlorinated or brominated ethylenic compound, and wherein said chlorinated or brominated ethylenic compound is optionally recycled to said step 1).

33. The process according to claim 3, wherein a distillation operation is carried out in said step 3) to separate said halogenoacetyl fluoride from said chlorinated or brominated ethylenic compound, and wherein said chlorinated or brominated ethylenic compound is optionally recycled to said step 1).

34. The process according to claim 3, wherein said fluorination of said halogenoacetyl fluoride is carried out in said step 4) by reaction of said halogenoacetyl fluoride with hydrofluoric acid with a fluorination catalyst present and with a molar ratio of said hydrofluoric acid to said halogenoacetyl fluoride between 1 and 20.

35. The process according to claim 2, being carried out to prepare trifluoroacetic acid from trifluoroacetyl fluoride obtained in said step 4), wherein:
in said step 1), trichloroacetyl chloride is prepared by photooxidation of tetrachloroethylene under conditions such that said tetrachloroethylene is converted to give trichloroacetyl chloride with a conversion of at most equal to 80%, resulting in a reaction mixture comprising the trichloroacetyl chloride and excess tetrachloroethylene,
in said step 2), the reaction mixture obtained in said step 1) is partially fluorinated by reacting said reaction mixture with hydrofluoric acid, to obtain a mixture of trichloroacetyl fluoride and said excess tetrachloroethylene,
in said step 3), the trichloroacetyl fluoride is separated from said excess tetrachloroethylene,
in said step 4), the trichloroacetyl fluoride obtained in said step 3) is fluorinated to give trifluoroacetyl fluoride by reaction of the trichloroacetyl fluoride and hydrofluoric acid, in a gas phase, with a chromium-based catalyst present, and
wherein the process further comprises:
step 5)—hydrolyzing the trifluoroacetyl fluoride obtained in said step 4) to form trifluoroacetic acid.

36. The process according to claim 3, being carried out to prepare trifluoroacetic acid, wherein:
in said step 1), trichloroacetyl chloride is prepared by photooxidation of tetrachloroethylene under conditions such that said tetrachloroethylene is converted to give trichloroacetyl chloride with a conversion of at most equal to 80%, resulting in a reaction mixture comprising the trichloroacetyl chloride and excess tetrachloroethylene,
in said step 2), the reaction mixture obtained in said step 1) is partially fluorinated by reaction of said reaction mixture with hydrofluoric acid, to obtain a mixture of trichloroacetyl fluoride and said excess tetrachloroethylene,
in said step 3), the trichloroacetyl fluoride is separated from said excess tetrachloroethylene,
in said step 4), the trichloroacetyl fluoride obtained in said step 3) is fluorinated to give trifluoroacetyl fluoride by reaction of the trichloroacetyl fluoride and hydrofluoric acid, in a gas phase, with a chromium-based catalyst present, and
in said step 5), the trifluoroacetyl fluoride obtained in said step 4) is hydrolyzed to form trifluoroacetic acid.

37. The process according to claim 6, wherein in said step 1), the conversion of said chlorinated or brominated ethylenic compound to said halogenoacetyl halide is between 60% and 75%.

38. The process according to claim 8, wherein the molar ratio of said hydrofluoric acid to said halogenoacetyl halide is between 1 and 5.

39. The process according to claim 9, wherein the temperature of said partial fluorination reaction in said step 2) is between 100° C. and 120° C.

40. The process according to claim 10, wherein said organic phase comprises from 60% to 70% by weight of said halogenoacetyl fluoride and from 40% to 30% by weight of said chlorinated or brominated ethylenic compound.

41. The process according to claim 12, wherein the molar ratio of said hydrofluoric acid to said halogenoacetyl fluoride is between 6 and 8.

42. The process according to claim 13, wherein said fluorination catalyst comprises an inorganic salt of chromium which is doped with a metal element selected from the group consisting of nickel, cobalt, magnesium, and zinc.

43. The process according to claim 14, wherein said fluorination catalyst comprises chromium which is doped with nickel or magnesium.

44. The process according to claim 17, wherein the temperature of said fluorination reaction of said step 4) is from 250° C. to 300° C.

45. The process according to claim 19, wherein the contact time in said fluorinaton reaction of said step 4) varies from 5 seconds to 50 seconds.

46. The process according to claim 20, wherein in said fluorinaton reaction of said step 4), the weight of substrate employed per weight of catalyst and per hour varies from 0.05 $h^{-1}$ to 0.5 $h^{-1}$.

47. The process according to claim 23, wherein the temperature of said gas stream is lowered to a value of from −20° C. to 0° C.

48. The process according to claim 25, wherein the base is sodium hydroxide or potassium hydroxide.

49. The process according to claim 26, wherein in said step 1), the conversion of said chlorinated or brominated ethylenic compound to said halogenoacetyl halide is from 60% to 75%.

50. The process according to claim 3, wherein in said step 1), the conversion of said chlorinated or brominated ethylenic compound to said halogenoacetyl halide is from 60% to 75%.

51. The process according to claim 30, wherein in said step 2), the molar ratio of said hydrofluoric acid to said halogenoacteyl halide is from 1 to 5.

52. The process according to claim 31, wherein in said step 2), the molar ratio of said hydrofluoric acid to said halogenoacteyl halide is from 1 to 5.

53. The process according to claim 34, wherein in said step 4), the molar ratio of said hydrofluoric acid to said halogenoacetyl fluoride is between 6 and 8.

* * * * *